(12) United States Patent
Greene et al.

(10) Patent No.: US 7,713,252 B2
(45) Date of Patent: May 11, 2010

(54) THERAPEUTIC ARTICLE INCLUDING A PERSONAL CARE COMPOSITION AND METHODS OF MAKING THE THERAPEUTIC ARTICLE

(75) Inventors: Sharon L. Greene, Canton, GA (US); Kaiyuan Yang, Cumming, GA (US); Shu-Ping Yang, Alpharetta, GA (US); Ning Wei, Roswell, GA (US); Jai Kyung, Alpharetta, GA (US); Jeffrey E. Fish, Dacula, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 11/300,601

(22) Filed: Dec. 14, 2005

(65) Prior Publication Data
US 2007/0135777 A1    Jun. 14, 2007

(51) Int. Cl.
*A61M 35/00*    (2006.01)
*A01N 25/34*    (2006.01)
(52) U.S. Cl. ............... 604/292; 604/289; 604/291; 424/402
(58) Field of Classification Search ......... 604/289–293, 604/294–302; 424/402, 443, 445–447, 449; 2/171.2
See application file for complete search history.

(56) References Cited

U.S. PATENT DOCUMENTS

| | | |
|---|---|---|
| 3,338,992 A | 8/1967 | Kinney |
| 3,341,394 A | 9/1967 | Kinney |
| 3,423,266 A | 1/1969 | Davies et al. |
| 3,485,706 A | 12/1969 | Evans |
| 3,502,538 A | 3/1970 | Petersen |
| 3,502,763 A | 3/1970 | Hartmann |
| 3,509,009 A | 4/1970 | Hartmann |
| 3,542,615 A | 11/1970 | Dobo et al. |
| 3,595,245 A | 7/1971 | Buntin et al. |
| 3,676,242 A | 7/1972 | Prentice |
| 3,692,618 A | 9/1972 | Dorschner et al. |
| 3,704,198 A | 11/1972 | Prentice |
| 3,715,251 A | 2/1973 | Prentice |

(Continued)

FOREIGN PATENT DOCUMENTS

EP    0764441 B1    3/1997

(Continued)

OTHER PUBLICATIONS

English language abstract for EP 0 764 441 B1 dated Mar. 26, 1997.

(Continued)

*Primary Examiner*—Melanie J Hand
(74) *Attorney, Agent, or Firm*—Dority & Manning, P.A.

(57) ABSTRACT

A therapeutic article includes a skin contact layer having a plurality of fibers forming a plurality of point-bearing surfaces configured for wear against a user's skin; a personal care composition disposed proximate the fibers; an external layer attached to the skin contact layer; and an intermediate layer interposed between the skin contact layer and the external layer, the intermediate layer being configured to activate the personal care composition, the external layer being configured to direct the activated personal care composition through the skin contact layer to treat the user.

27 Claims, 7 Drawing Sheets

U.S. PATENT DOCUMENTS

| | | | |
|---|---|---|---|
| 3,802,817 A | 4/1974 | Matsuki et al. | |
| 3,849,241 A | 11/1974 | Butin et al. | |
| 3,855,046 A | 12/1974 | Hansen et al. | |
| 4,041,203 A | 8/1977 | Brock et al. | |
| 4,100,324 A | 7/1978 | Anderson et al. | |
| 4,323,534 A | 4/1982 | DesMarais | |
| 4,340,563 A | 7/1982 | Appel et al. | |
| 4,587,110 A | 5/1986 | Potter et al. | |
| 4,655,760 A | 4/1987 | Morman et al. | |
| 4,657,802 A | 4/1987 | Morman | |
| 4,663,220 A | 5/1987 | Wisneski et al. | |
| 4,720,252 A | 1/1988 | Appel et al. | |
| 4,720,415 A | 1/1988 | Wielen et al. | |
| 4,766,029 A | 8/1988 | Brock et al. | |
| 4,781,966 A | 11/1988 | Taylor | |
| 4,789,699 A | 12/1988 | Kieffer et al. | |
| 4,803,117 A | 2/1989 | Daponte | |
| 4,818,464 A | 4/1989 | Lau | |
| 4,828,556 A | 5/1989 | Braun et al. | |
| 4,834,738 A | 5/1989 | Kielpikowski et al. | |
| 4,965,122 A | 10/1990 | Morman | |
| 4,981,747 A | 1/1991 | Morman | |
| 5,093,422 A | 3/1992 | Himes | |
| 5,114,781 A | 5/1992 | Morman | |
| 5,116,662 A | 5/1992 | Morman | |
| 5,145,727 A | 9/1992 | Potts et al. | |
| 5,167,655 A * | 12/1992 | McCoy | 604/396 |
| 5,169,706 A | 12/1992 | Collier et al. | |
| 5,178,931 A | 1/1993 | Perkins et al. | |
| 5,188,885 A | 2/1993 | Timmons et al. | |
| 5,226,992 A | 7/1993 | Morman | |
| 5,304,599 A | 4/1994 | Himes | |
| 5,332,613 A | 7/1994 | Taylor et al. | |
| 5,336,545 A | 8/1994 | Morman | |
| 5,354,514 A | 10/1994 | Satake et al. | |
| 5,382,400 A | 1/1995 | Pike et al. | |
| 5,389,202 A | 2/1995 | Everhart et al. | |
| 5,464,688 A | 11/1995 | Timmons et al. | |
| 5,591,510 A | 1/1997 | Junker et al. | |
| 5,869,072 A * | 2/1999 | Berry | 424/402 |
| 6,090,403 A | 7/2000 | Block et al. | |
| 6,402,991 B1 * | 6/2002 | Itakura et al. | 252/500 |
| 6,420,625 B1 | 7/2002 | Jones et al. | |
| 6,647,549 B2 | 11/2003 | McDevitt et al. | |
| 6,683,228 B1 * | 1/2004 | Pacheco, Sr. | 604/361 |
| 7,033,645 B2 * | 4/2006 | Gatto et al. | 427/374.1 |
| 7,108,440 B1 * | 9/2006 | Gruenbacher et al. | 401/132 |
| 2002/0006886 A1 | 1/2002 | Beerse et al. | |
| 2004/0116018 A1 | 6/2004 | Fenwick | |
| 2004/0225049 A1 * | 11/2004 | Komuro | 524/403 |
| 2004/0247654 A1 | 12/2004 | Asmus et al. | |
| 2005/0084438 A1 | 4/2005 | Do et al. | |
| 2005/0085144 A1 | 4/2005 | MacDonald et al. | |
| 2005/0112085 A1 | 5/2005 | MacDonald et al. | |
| 2005/0125923 A1 | 6/2005 | Benjamin et al. | |
| 2006/0226378 A1 * | 10/2006 | Yabiku | 250/504 R |

FOREIGN PATENT DOCUMENTS

| | | |
|---|---|---|
| GB | 1217892 | 10/1973 |
| WO | WO 9212695 | 8/1992 |
| WO | WO 9956796 A1 | 11/1999 |
| WO | WO 0108657 A2 | 2/2001 |
| WO | WO 03092885 | 11/2003 |
| WO | WO 2005039655 | 5/2005 |
| WO | WO 2005039656 | 5/2005 |
| WO | WO 2005039784 | 5/2005 |

OTHER PUBLICATIONS

Lindsay, et al, U.S. Appl. No. 11/247,768, filed Oct. 11, 2005, Micro Powered Warming Container.

Yang, et al., U.S. Appl. No. 11/118,078, filed Apr. 29, 2005, Finger Wipe with Improved Seam Structure.

* cited by examiner

THERAPEUTIC ARTICLE INCLUDING A PERSONAL CARE COMPOSITION AND METHODS OF MAKING THE THERAPEUTIC ARTICLE

BACKGROUND OF THE INVENTION

A variety of therapeutic articles are used to treat various ailments, injuries and the like. However, a need exists for personal care articles, which can be used in home spa applications. The personal care articles need to be modular and have activatable personal care compositions to provide a variety of therapeutic benefits to a user.

SUMMARY OF THE DISCLOSURE

Objects and advantages of the invention will be set forth below in the following description, or may be obvious from the description, or may be learned through practice of the invention.

In one embodiment of the present invention, a therapeutic article includes a permeable skin contact layer having a plurality of point-bearing surfaces with indentations therebetween, the point-bearing surfaces being configured for wear against a user's skin; a personal care composition disposed proximate the fibers, the personal care composition having an active state and an inactive state; an external layer attached to the skin contact layer, the external layer and the skin contact layer defining a flush seam therebetween; and an intermediate layer interposed between the skin contact layer and the external layer, the intermediate layer being configured to activate the personal care composition from the inactive state, the external layer being configured to direct the activated personal care composition through the skin contact layer to treat the user. In this aspect of the invention, the skin contact layer can include elastomeric fibers or non-extensible fibers. Still further, the skin contact layer can be an extensible nonwoven material.

The personal care composition can be an emollient, a petrolatum, a mineral oil, a lipid, an herb, an herbal extract, a skin softener, an aloe, an anti-inflammatory product, an essential oil, a vitamin solution, a mineral solution and combinations thereof.

In particular embodiments, the external layer is a reflective layer, and the intermediate layer is a heating layer. More particularly, the intermediate layer can be a Far-IR emitting layer or a Near-IR absorbing layer. Still further, the intermediate layer can be a cooling layer.

A pocket can be located adjacent the skin contact layer, the pocket being configured to contain the personal care composition. More particularly, the therapeutic article can include a holder located adjacent the skin contact layer, the holder being configured to contain the personal care composition. The holder in this aspect can be a pocket, a pouch, a bag and combinations of these devices.

The therapeutic article in this aspect can further include an odor control layer interposed between the skin contact layer and the external layer. The odor control layer can be a negatively or positively charged odor control layer. The odor control layer can also be a charcoal-containing odor control layer.

The therapeutic article may include seams between various materials. In this regard, the seams may be flush seams of about 500 microns in width and about 500 microns in height, preferably less than about 300 microns in width and about 300 microns in height, and most preferably less than 50 microns in width and about 50 microns in height.

The therapeutic article can further include means for holding the skin contact layer against the skin such as selected a snap, a hook, a pin, an adhesive, a button and hole arrangement, a hook and loop fastening arrangement, an extensible-retractive force and combinations of these devices and forces.

In a further embodiment of the invention, a therapeutic article can include a skin contact layer being configured for wear against a user's skin; a pocket disposed proximate the skin contact layer; a personal care composition disposed in the pocket, the personal care composition having an active state and an inactive state; an external layer attached to the skin contact layer; a heating layer interposed between the skin contact layer and the external layer, the heating layer being configured to generate heat to activate the personal care composition from the inactive state, the external layer being configured to direct the personal care composition in the active state through the skin contact layer to treat the skin; and an odor-controlling layer interposed between the skin contact layer and the external layer to control an unpleasant odor emanating from the personal care composition. The therapeutic article in this aspect can be an elastomeric article and can be a facial mask, a wrap, a brace, an underarm insert, a patch, a glove, a sock, an undergarment, a sleeve and a girdle. The heating layer can be a Far-IR emitting layer or a Near-IR absorbing layer.

Also in this aspect of the invention, the personal care composition can be selected from the an emollient, a petrolatum, a mineral oil, a lipid, an herb, an herbal extract, a skin softener, an aloe, an anti-inflammatory product, an essential oil, a vitamin solution, a mineral solution and combinations of these ingredients. The essential oil, for example, can be selected from a lavender extract, a tea tree oil extract, a lemon grass extract, a eucalyptus extract, a clove extract and a thyme extract.

In a further embodiment of the invention, a method of forming a therapeutic article includes the steps of providing a skin contact layer, which may be a nonwoven material, configured for wear against the user's skin; disposing a personal care composition proximate the skin contact layer; substantially seamlessly attaching an external layer to the skin contact layer; and interposing an intermediate layer between the skin contact layer and the external layer, the intermediate layer being configured to activate the personal care composition, the external layer being configured to direct the activated personal care composition through the skin contact layer to treat the user. In this method, the skin contact layer may be elastomeric or non-extensible. The skin contact layer may also be a woven fiber.

Also in this aspect of the invention, the layers can be attached by an ultrasonic bonder to define a flush seam. The flush seam is less than about 300 microns in width and about 300 microns in height, preferably less than about 50 microns in width and about 50 microns in height Further, the intermediate layer according to this method is configured to generate heat to heat the personal care composition. Alternatively, or additionally, the intermediate layer can be configured to provide cooling to treat the user.

Various other features and aspects of the present invention are discussed in greater detail below.

BRIEF DESCRIPTION OF THE DRAWINGS

A full and enabling disclosure of the present invention, including the best mode thereof, directed to one of ordinary skill in the art, is set forth in the specification, which makes reference to the appended drawings, in which.

DETAILED DESCRIPTION OF THE DISCLOSURE

Figure 1:
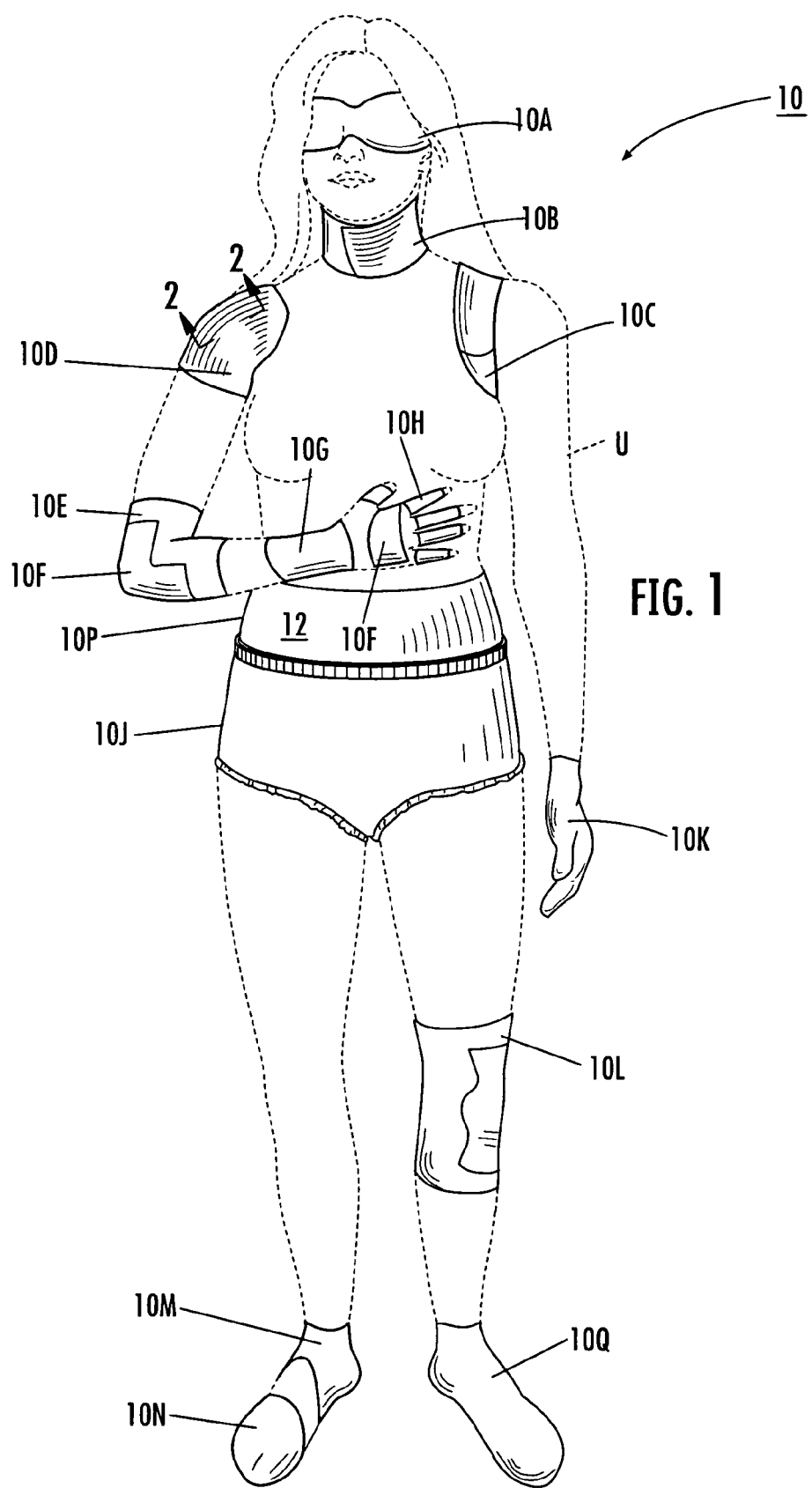
FIG. 1 is an elevational view of a user wearing various personal care articles according to a variety of embodiments of the present invention.

Detailed reference will now be made to the drawings in which examples embodying the present invention are shown. Repeat use of reference characters in the drawings and detailed description is intended to represent like or analogous features or elements of the present invention.

The drawings and detailed description provide a full and detailed written description of the invention and the manner and process of making and using it, so as to enable one skilled in the pertinent art to make and use it. The drawings and detailed description also provide the best mode of carrying out the invention. However, the examples set forth herein are provided by way of explanation of the invention and are not meant as limitations of the invention. The present invention thus includes modifications and variations of the following examples as come within the scope of the appended claims and their equivalents.

DEFINITIONS

As used herein, the following terms have the specified meanings, unless the context demands a different meaning, or a different meaning is expressed; also, the singular generally includes the plural, and the plural generally includes the singular unless otherwise indicated. For example, as used herein, the term "member" when used in the singular can refer to a single element or a plurality of elements.

Words of degree, such as "about", "substantially", and the like are used herein in the sense of "at, or nearly at, when given the manufacturing and material tolerances inherent in the stated circumstances" and are used to prevent the unscrupulous infringer from unfairly taking advantage of the invention disclosure where exact or absolute figures are stated as an aid to understanding the invention.

As used herein, the term "sheet" refers to a layer, which may be a film, foam, or nonwoven web.

The terms "elastic composite" or "elastic laminate", as used herein, refers to a material having at least one elastic material joined to at least one sheet material. A composite elastic laminate is disclosed, for example, in U.S. Pat. No. 4,720,415 to Vander Wielen et al., which is incorporated herein in its entirety by reference thereto.

As used herein, the term "coform web" refers to a material produced by combining separate polymer and additive streams into a single deposition stream in forming a nonwoven web. Such a process is taught, for example, by U.S. Pat. No. 4,100,324 to Anderson et al., which is hereby incorporated by reference.

As used herein, the term "spunbonded fibers" refers to small diameter fibers formed by extruding a molten thermoplastic material as filaments from a plurality of fine, usually circular, capillaries of a spinerette with the diameter of the extruded filaments then being rapidly reduced as by, for example, eductive stretching or other well-known spunbonding mechanisms.

As used herein, the term "meltblown fibers" means fibers formed by extruding a molten thermoplastic material through a plurality of fine, usually circular, die capillaries as molten thermoplastic material or filaments into a high velocity gas (e.g. air) stream which attenuates the filaments of molten thermoplastic material to reduce their diameter, which may be to microfiber diameter. Thereafter, the meltblown fibers are carried by the high velocity gas stream and are deposited on a collecting surface to form a web of randomly disbursed meltblown fibers.

As used herein, the term "neck-bonded" refers to an elastic member being bonded to a non-elastic member while the non-elastic member is extended in the machine direction creating a necked material.

As used herein, the term "neck-bonded laminate" (NBL) refers to a composite material having at least two layers in which one layer is a necked, non-elastic layer and the other layer is an elastic layer thereby creating a material that is elastic in the cross direction. Examples of neck-bonded laminates are described in U.S. Pat. Nos. 5,226,992; 4,981,747; 4,965,122; and 5,336,545, all to Morman, all of which are incorporated herein by reference thereto.

As used herein, the term "stretch-bonded" refers to a composite material having at least two layers in which one layer is a gatherable layer and the other layer is an elastic layer. The layers are joined together when the elastic layer is in an extended condition so that upon relaxing the layers, the gatherable layer is gathered.

"Neck stretch-bonded" laminate refers to a laminate made from the combination of a neck-bonded laminate and a stretch-bonded laminate. Examples of necked stretch bonded laminates are disclosed in U.S. Pat. Nos. 5,114,781 and 5,116,662, which are incorporated herein in their entirety by reference thereto for all purposes.

As used herein, the term "breathable" means pervious to water vapor and gases. In other words, "breathable barriers" and "breathable films" allow water vapor to pass therethrough, but are substantially impervious to liquid water. For example, "breathable" can refer to a film or laminate having water vapor transmission rate (WVTR) of at least about 300 g/m$^2$/24 hours measured using ASTM Standard E96-80, upright cup method, with minor variations as described in the following Test Procedure.

As used herein, a "liquid impermeable layer" refers to any material that is relatively impermeable to the transmission of fluids, i.e. a fabric having a liquid impermeable layer can have a blood strikethrough ratio of 1.0 or less according to ASTM test method 22.

"Attached" and "joined" refers to the bonding, adhering, connecting, and any other method for attaching or joining two elements. Two elements will be considered to be attached or joined together when they are bonded directly to one another or indirectly to one another, such as when each is directly attached to an intermediate element.

"Extendable" or "extensible" means that property of a material or composite by virtue of which it stretches or extends in the direction of an applied biasing force by at least about 25% of its relaxed length. An extendable material does not necessarily have recovery properties. For example, an elastomeric material is an extendable material having recovery properties. A meltblown web may be extendable, but not have recovery properties and, thus, be a non-elastic material.

"Non-extensible" refers to a material that does not stretch or extend by at least about 25% of its relaxed length without fracture upon application of a biasing force.

As used herein, the term "pocket" can mean an indentation, a depression, a hole, a pouch, a slot, a cavity and any combinations of these.

Various aspects and embodiments of the invention will be described in the context of one or more materials for disposable or reusable articles such as wraps or bandages, gloves, socks, insoles, facial masks, underarm inserts, patches, undergarments, girdles and the like. It should be appreciated that this is for illustrative purposes only and that the invention is not limited to any particular article or disposable or reusable articles in general. The materials according to the invention may have beneficial uses in any number of applications, such as protective medical clothing, drapes, gowns and the like. Thus, it is to be understood by one of ordinary skill in the art that the present discussion is a description of exemplary embodiments only and is not intended as limiting the broader aspects of the present invention.

In general, the figures show various embodiments of a personal care product or therapeutic article for use by a consumer and processes for making the therapeutic article. The therapeutic article generally includes a personal care composition, which is used to treat skin, to deliver aromatherapy, and to deliver a medicinal or herbal treatment, or to deliver combinations of these and other health and comfort treatments. Although the figures generally show a unitary elastomeric article that conforms to a body part of a user, the skilled artisan will appreciate that nonwoven or woven materials having varying degrees of extensibility, or that are substantially non-extensible, can be provided in the form of a loose fitting drape or gown according to various aspects of the invention. Further, it will be understood that articles according to the invention can be made flat in the form of an open belt or wrap, which can be placed on or wrapped around a desired body part; e.g., an arm or knee. Such flat, belt-like articles may be desirable for high-speed manufacturing processes. As described in greater detail below, these flat, belt-like articles can have adjustment mechanisms such as hook and loop fasteners for a user to adjust a size and comfort level of the article. Thus, the skilled artisan will appreciate that the present invention is not limited to the examples shown in the drawings.

With more particular reference now to FIG. 1, a consumer or user U is shown wearing a plurality of therapeutic spa items designated in general by the element number 10. The therapeutic spa items 10 broadly include by way of example but without limitation a facial wrap or mask 10A, a neck brace or wrap 10B, an underarm insert 10C, a shoulder wrap 10D, a band or sleeve 10E, a plurality of bandages or patches 10F, a wrist wrap 10G, a plurality of finger gloves 10H, a girdle or waist wrap 10P, an undergarment 10J, a glove 10K, a knee brace or wrap 10L, an ankle wrap 10M, a toe glove 10N and a sock 10Q. As shown, the various spa items 10 each include an external layer 12 labeled, for example, on the girdle 10I. The external layer 12 and additional components of the therapeutic spa items 10 are described in greater detail below with respect to the remaining figures.

Figure 2:
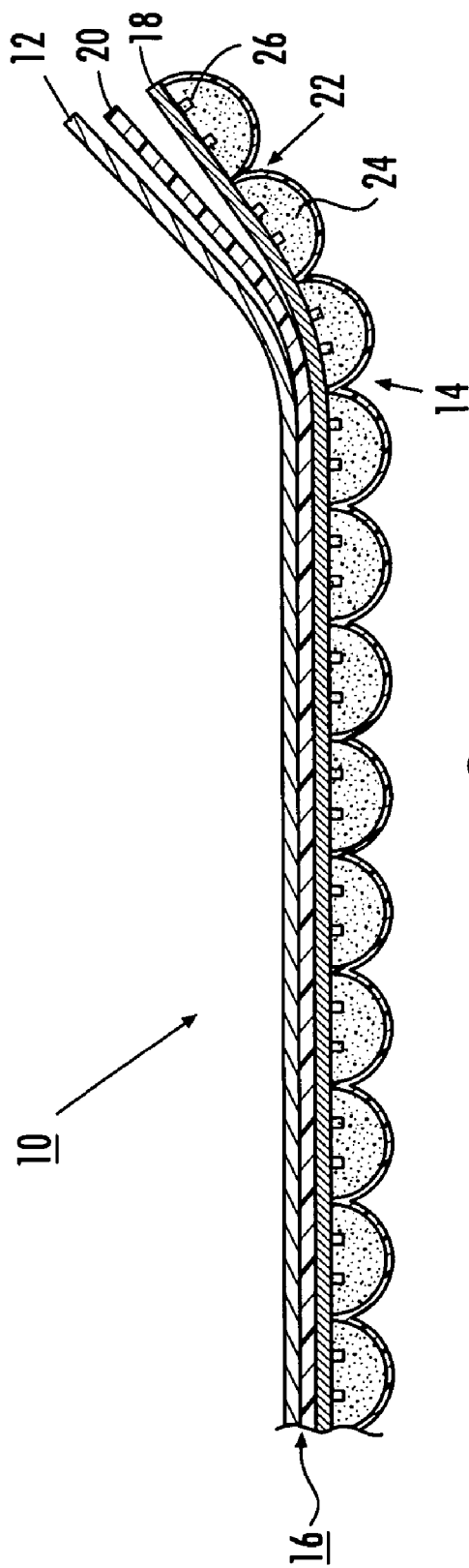
FIG. 2 is a partial cross sectional view of a portion of one of the embodiments taken along line 2-2 in FIG. 1.

FIG. 2 shows a variety of layers in a cross section of the shoulder wrap 10D of FIG. 1. The skilled artisan will instantly appreciate that the cross section is taken from the shoulder wrap 10D merely for the sake of discussion and that other of the therapeutic spa items 10 shown in FIG. 1 can include like or similar layers. As shown, the cross section of the shoulder wrap 10D includes the external layer 12 briefly introduced above and a skin contact layer 14. A plurality of intermediate layers 16 is disposed between the external layer 12 and the skin contact layer 14. In this example, the external layer 12 is a reflective layer to contain heat and also to absorb ambient or radiant heat to deliver the heat to the user's skin. However, the external layer 12 can be, for instance, an extensible, non-reflective material and is not limited to the example in FIG. 2.

As further shown in FIG. 2, the skin contact layer 14 includes a plurality of pockets or pouches 22 (also referred to herein as indentations, openings, recesses and the like). The pockets 22 can hold a variety of ingredients, which form a personal care composition 24. The personal care composition 24 can be an emollient, petrolatum, mineral oil, lipid, herb, herbal extract, skin softener, aloe, anti-inflammatory product, essential oil, vitamin solution, mineral solution and combinations of these and other ingredients as introduced above. For instance, the personal care composition 24 can include but is not limited to herbs for joint health/pain relief such as Tangkuei Root, Sichuan Lovage Root, Sichuan Aconite, Frankincense Gum-resin, Ginger, Wild Aconite and Safflower. The ingredients can also be anti-inflammatory botanicals such as *Boswillia*, Tumeric, Devil's Claw, Ginger, Black Spruce, *Allium cepa, Allium Satinum, Camillia sinensis,* evening primrose, flax seeds oil, and *Tanacetum parthenum*. The essential oil can include but is not limited to lavender extract, tea tree oil extract, lemon grass extract, eucalyptus extract, clove extract, thyme extract and combinations of these and other extracts. These and other ingredients suitable for use in or as personal care composition 24 are described in further detail below with respect to specific embodiments of the invention.

The skin contact layer 14 shown in FIG. 2 can also include a textured surface 26 such as tufts made, for instance, by coform processes described above. The textured surface 26 can be disposed between the pockets 22 as shown and described in greater detail with respect to FIG. 3 below.

FIG. 2 further shows one or more of the intermediate layers 16 as a heating layer 18. The user U can activate the heating layer 18 electrically or electrochemically, or the heating layer 18 can be activated by radiant heat. For instance, the heating layer 18 can be a Far-IR emitting layer to radiate Far-IR light at room temperature or a Near-IR absorbing layer having a high absorbency in the Near IR-region.

By way of example and without limitation, ceramic materials can be used to produce far-IR-radiating materials for use as the heating layer 18. For instance, a ceramic composition of about 52.5-70 wt % $SiO_2$ and about 20-47 wt % $Al_2O_3$ is described in Japanese Patent No. 1822582 as having suitable Far-IR-radiating characteristics. Also by way of example and without limitation, U.S. Pat. No. 5,354,514 describes a Near IR-absorbing composition, which can be used as the heating layer 18. This exemplary Near IR-absorbing composition includes a thioamide compound and at least one compound selected from a member consisting of a copper compound and a lead compound, a Near IR-absorbing material including both compounds, and a product containing the composition or the material in which the material is obtained by heating a composition containing the thioamide compound and the copper compound and/or the lead compound. A further non-limiting example suitable for use as a heating layer or element in or as the heating layer 18 is a heating plate powered by a micro fuel cell device described by Lindsay et al. in U.S. patent application Ser. No. 11/247,768, filed Oct. 11, 2005, which is incorporated herein by reference thereto.

Continuing with reference to FIG. 2 another of the intermediate layers 16 can be an odor control layer 20, which can be combined with the heating layer 18. The odor control layer 20 can be a unitary layer such as a charcoal-packed layer, or the layer 20 can be a loose powder configuration, made also of charcoal or another odor absorbing material. By way of example, odor control technology that may be incorporated in the present invention is described in WO 2003092885A1; WO 2005039655A1; WO 2005039656A1; and WO 2005039784A2, all incorporated herein by reference.

Figure 3:
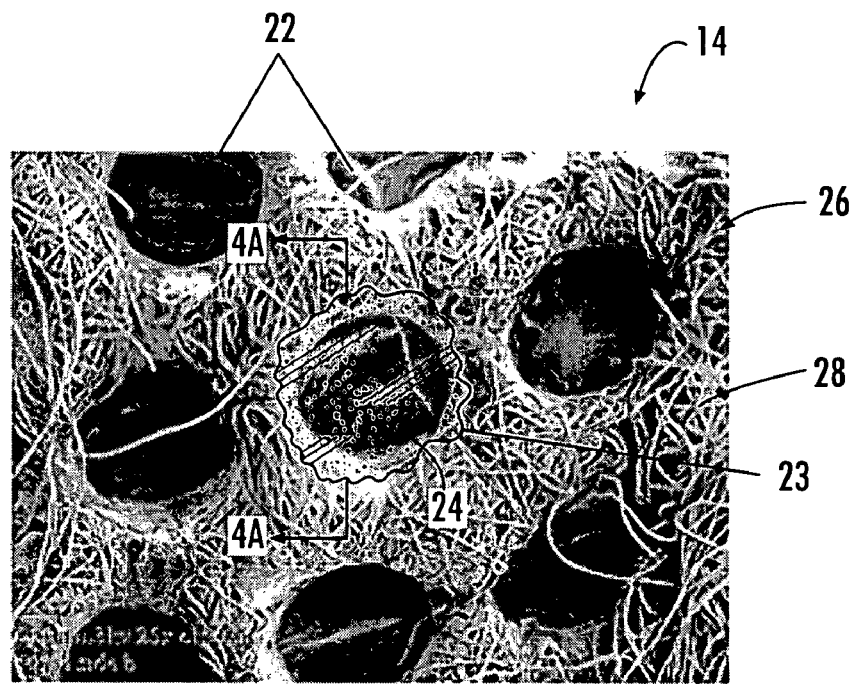
FIG. 3 is a scanning electron micrograph of an embodiment of a skin contact layer that may be used in an article according to the invention.
Figure 4A:
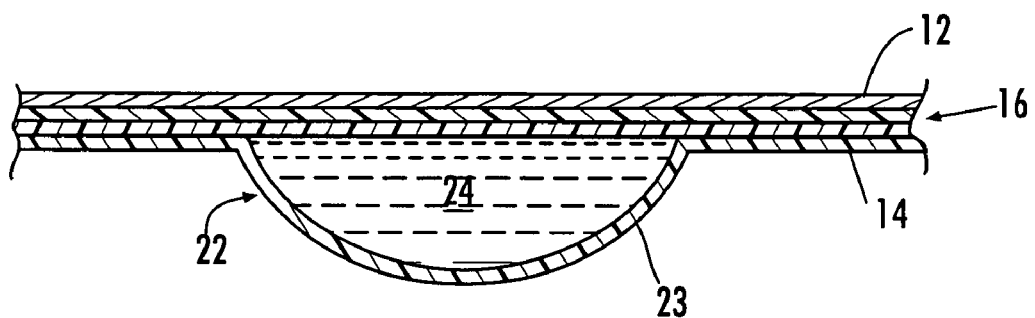
FIG. 4A is a sectional depiction taken along line 4A-4A in FIG. 3.

With reference now to FIGS. 2, 3 and 4A, the pockets 22 can be formed by bonding using a conventional bonder or pin roller. As shown, one or more of the ingredients of the personal care composition 24 described above can be contained in the pockets 22. The pockets 22 may include a layer 23 to contain the personal care composition 24. Thus, in this aspect of the invention, the pocket 22 and the layer 23 can be an activated by the user U when the user U is ready to use the article. The layer 23 can be, for instance, a gelatin coating that can be broken by a compressive force or by mechanical tearing to deliver the ingredients of the personal care composition 24 to the user's skin. Alternatively, or in addition to the compressive or mechanical forces, the heating layer 18 can melt the gelatin layer 23 to allow the ingredients to seep from the pockets 22 in a direction of the skin of the user U.

FIG. 3 most clearly shows the textured surface 26 briefly introduced above. The textured surface 26 in this example is a plurality of nonwoven fibers 28 around and into which the ingredients of the personal care composition 24 are embedded, soaked, coated, dried and the like. A well-known method for forming a textured surface such as the textured surface 26 in a nonwoven material is a thermal bonding process in which raised, unbonded (or lightly bonded) areas are surrounded by bonded regions. A textured material formed by such a process may be desired as the outer cover layer 12 in the articles 10 according to the invention. For example, in the embodiments of FIGS. 4B, 4C and 10A discussed below, the outer section panel 12 is a thermally bonded material having raised unbonded regions or tufts surrounded by bonded regions.

Figure 4B:
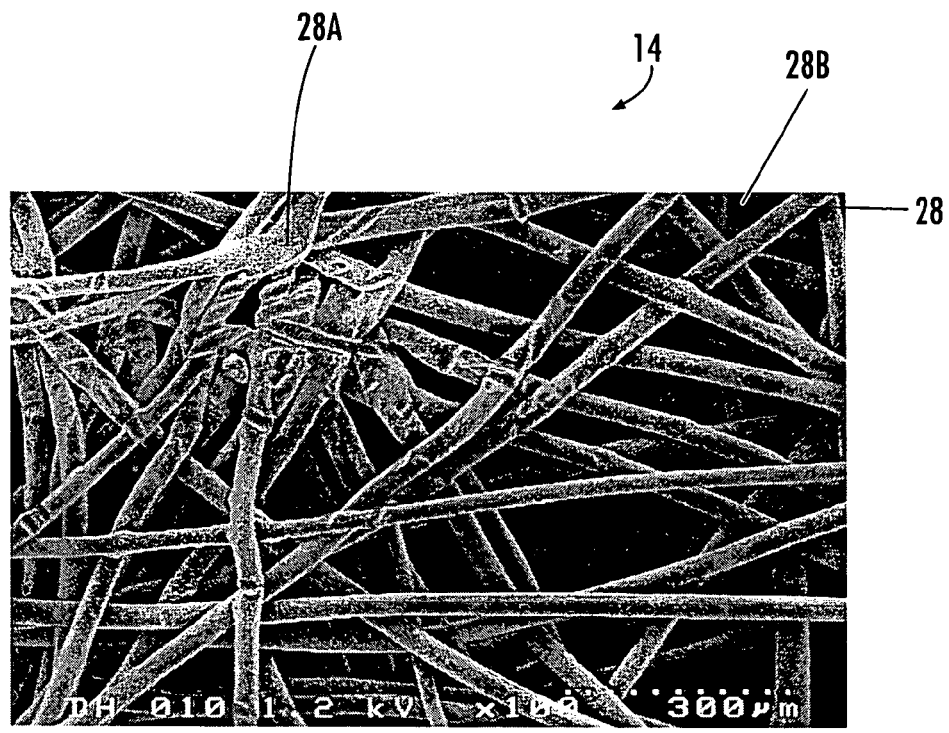
FIG. 4B is a scanning electron micrograph of fibers in a web of material for forming an article such as in FIG. 1 prior to adding a personal care composition.
Figure 4C:
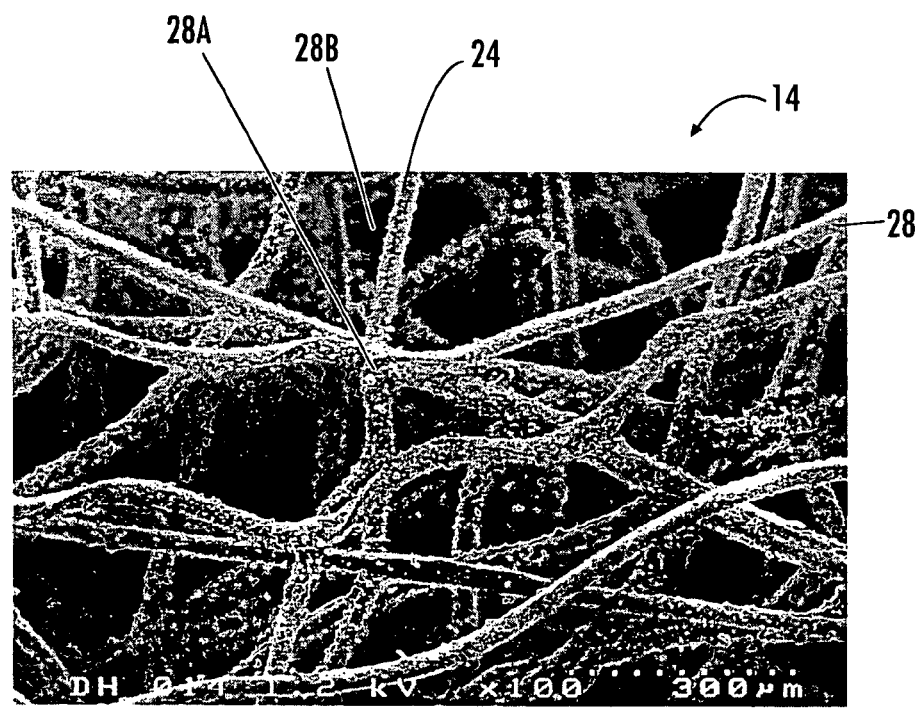
FIG. 4C is a scanning electron micrograph of an example of the present invention particularly showing the fibers as in FIG. 4B including a personal care composition.

As shown in FIGS. 4B and 4C, a microscopic view of the fibers 28 of the skin contact layer 14 is shown in which a plurality of point bearing surfaces 28A of the fibers 28 are surrounded by a plurality of openings, recesses or indentations 28B. FIG. 4C particularly shows the point bearing surfaces 28A and indentations 28B coated or infused with the ingredients 24 as described above. Therefore, in this example, the fibers 28 themselves carry the ingredients instead of, or in addition to, the pockets 22 described above. It will be appreciated that in one aspect of the invention, neck-bonded laminates (NBL) will be used rather than, for example, stretch-bonded laminates when the ingredients 24 are an externally applied liquid formulation or treatment since an NBL film barrier layer can contain the liquid ingredients 24 without leakage.

At least one additional personal care composition similar to the personal care composition 24 described above can be topically or externally applied to fibers, fabrics, films and foams that already include an internal personal care composition 24 to provide an additional skin treatment benefit and/or to enhance the existing skin treatment benefit. For example, a first personal care composition, such as dimethicone, can be melt blended into a thermoplastic resin and then used to form a nonwoven fabric or fibers that make up a nonwoven fabric to allow increased loading and retention of a second, other personal care composition, such as clay. Clay particles can be coated or otherwise deposited on the surface of the fibers or nonwoven fabric. In another example, a lipid can be melt blended into a thermoplastic composition that is formed into fibers, nonwoven fabrics or films. Then, clay particles or a botanical extract can be applied to the surface of the fiber, fabric or film to provide a fiber, fabric or film with more than one skin treatment benefit, a first skin treatment benefit from the lipid and a second skin treatment benefit from the clay or botanical extract or the clay and botanical extract can be co-administered to provide fiber, fabric or film with multiple skin treatment benefits. It is believed that the addition of dimethicone significantly enhances clay capture efficiency on the surface of the fiber, fabric, film, foam or other substrate that includes dimethicone as an internal additive. Thus, in one embodiment the present invention provides a method of providing clay particles on the surface of a substrate such as a nonwoven fabric that does not require the incorporation of the clay particles into a semi-solid such as an ointment.

The additional personal care composition(s) may be topically applied or otherwise added to the surface of the fibers, fabrics, films or foams by: (a) electrostatic pinning of particles of a personal care composition or particles that include at least one personal care composition on at least a portion of the outer surface of the fiber, fabric, porous film or foam; (b) spraying a solution, emulsion or other mixture that includes the at additional personal care composition on at least a portion of the outer surface of the fiber, fabric, porous film or foam; (c) heating at least a portion of the outer surface of the fiber, fabric, porous film or foam and then depositing particles that include the additional personal care composition on at least a portion of the outer surface of the fiber, fabric, porous film or foam; (d) depositing particles that include the additional personal care composition on at least a portion of the outer surface of fiber, fabric, film or foam and then heating at least the portion of the outer surface of the fiber, fabric, film or foam; and/or (e) coating or attaching the additional personal care composition or a solution or mixture that includes the additional personal care composition on at least a portion of the outer surface of fiber, fabric, film or foam.

The skilled artisan will appreciate that personal care compositions, such as the above-described personal care composition 24, that are not thermally stable or that do not bloom to the surface should be topically applied to the surface of a fiber, fabric, film or foam instead of incorporating the personal care composition as an internal melt additive. The topically applied compositions may be in particulate form. Suggested personal care compositions that may be topically applied include, but are not limited to: clays including both natural and synthetic clays such as kaolin and LAPONITE clays, and aluminum silicates; aluminum hydroxides; talcs; zinc oxides; zinc acetates; zinc carbonates; silver oxides; titanium oxides; talc particles; boron nitride particles; cornstarch; polylactic acid; biopolymers such as hyaluronic acid, chitosan and chemically-modified sulfated chitosans; botanical extracts, such as chamomile, lavender, teas that include green, black and white teas, aloe vera, echinacea, yucca, willow herb and other herbal extracts; moisturizing agents and humectants such as glycerin; D-panthenol; emollients such as triglycerides and Di-PPG-3 myristyl ether adipate; skin treatment ingredients that help prevent skin damage or that temporarily protect the skin barrier such as fatty acids, ceramides, lanolin, butters such as cocoa butter, oils such as shark liver oil; vitamins such as Vitamin A, $B_5$, $B_{12}$, D and E; anti-inflammatory agents such as β-glucan, β-glucan derivatives, licorice extract and oat extracts; astringents such as witch hazel extract; and agents that relieve inflamed or irritated skin such as allantoin. Personal care compositions such as fatty acids and fatty alcohols; skin protectants that help prevent skin damage or that temporarily protect the skin barrier such as lanolin, butters such as cocoa butter, oils such as shark liver oil; agents that relieve inflamed or irritated skin such as allantoin and witch hazel; and enzyme inhibitors can be applied either through internal melt addition or through topical application as long as the personal care composition(s) can withstand melt processing without significant degradation or is incorporated in a manner in which the additive survives melt processing without significant degradation and is available for skin treatment.

Still other skin health additives that may be applied to the exterior surface include, but are not limited to, alumina, hydroxyapatite, derivatized carbohydrates such as cellulose, cyclodextrins, silica, activated charcoal, analgesics, antihistamines and anitoxidants. Still yet other potential additives include enzyme inhibitors, vitamins, chelating agents emollients, preservatives, buffering compositions, antimicrobials and so forth. The efficacy of a personal care composition that does not readily migrate to the surface if used as an internal melt additive, for example a particulate personal care composition, can be enhanced by topically applying the personal care composition instead of incorporating the personal care composition internally or in the melt. The skin health additive, for example alumina or silica, can be derivatized to enhance or impart affinities for the charged or hydrophobic materials.

As mentioned, one suggested class of particulate personal care compositions for topical application include clay particles that may be coated onto or otherwise topically applied to the fibers to absorb water or sequester irritants. Clay particles can be applied by electrostatic pinning after the Fiber Draw Unit (FDU) and before the bonder, spraying before the bonder, depositing on activated binder fibers in the bonder or after the bonder and by methods including, but not limited to, slot coating, printing and spraying. The particles are preferably blown onto the stream of particles shortly after the fibers leave an extrusion nozzle and the particles may be given an electrostatic charge prior to contacting the fibers, which helps to separate the particles in the fabric. An electrostatic charge is desirably applied to the particles to promote individual particle separation in the composite, as gravity drops the particles into the air stream.

Further examples of fiber production and personal care composition additives are described in U.S. application Ser. No. 10/322,007, filed Dec. 17, 2002, and entitled "Method of Making Fibers, Nonwoven Fabrics, Porous Films and Foams that Include Personal care compositions", incorporated herein by reference without limitation.

Figure 5:
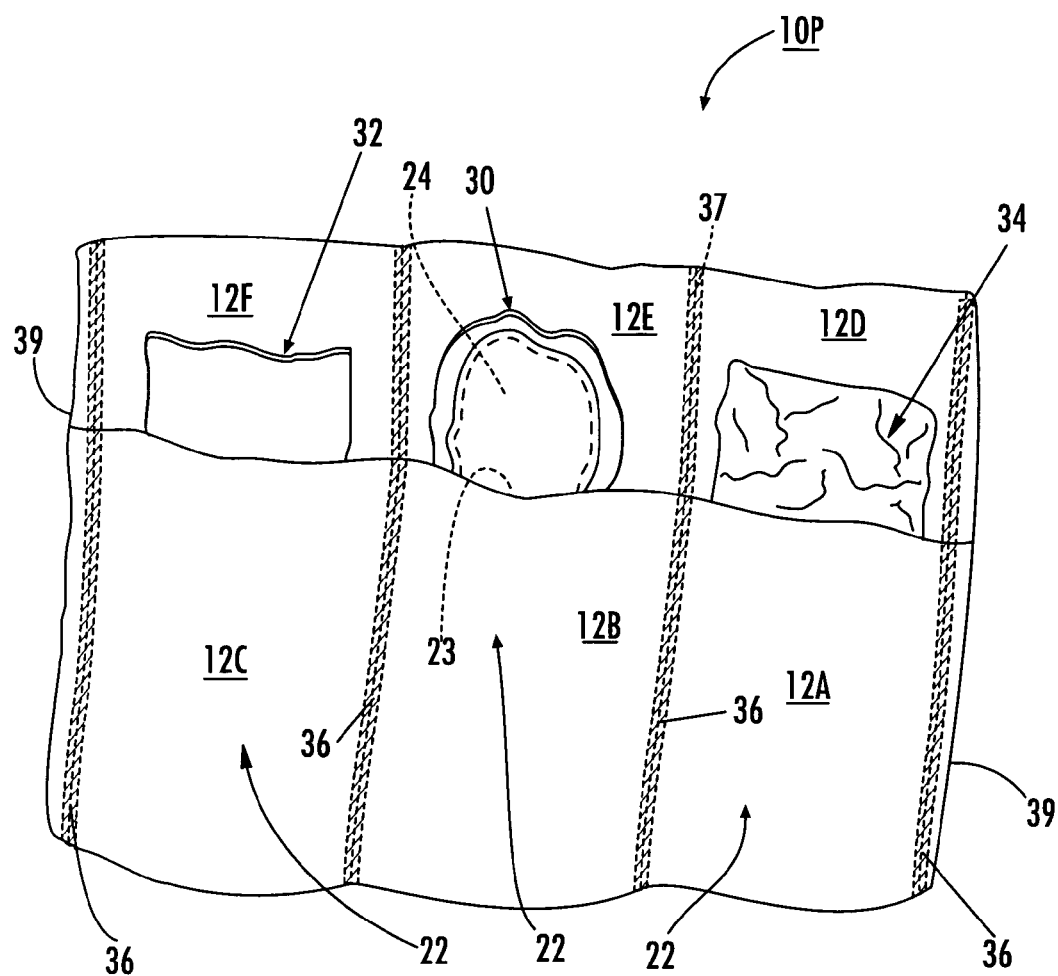
FIG. 5 is a plan view of a personal care article as in FIG. 1 including a therapeutic bag and a cooling pad according to other aspects of the invention.
Figure 6:
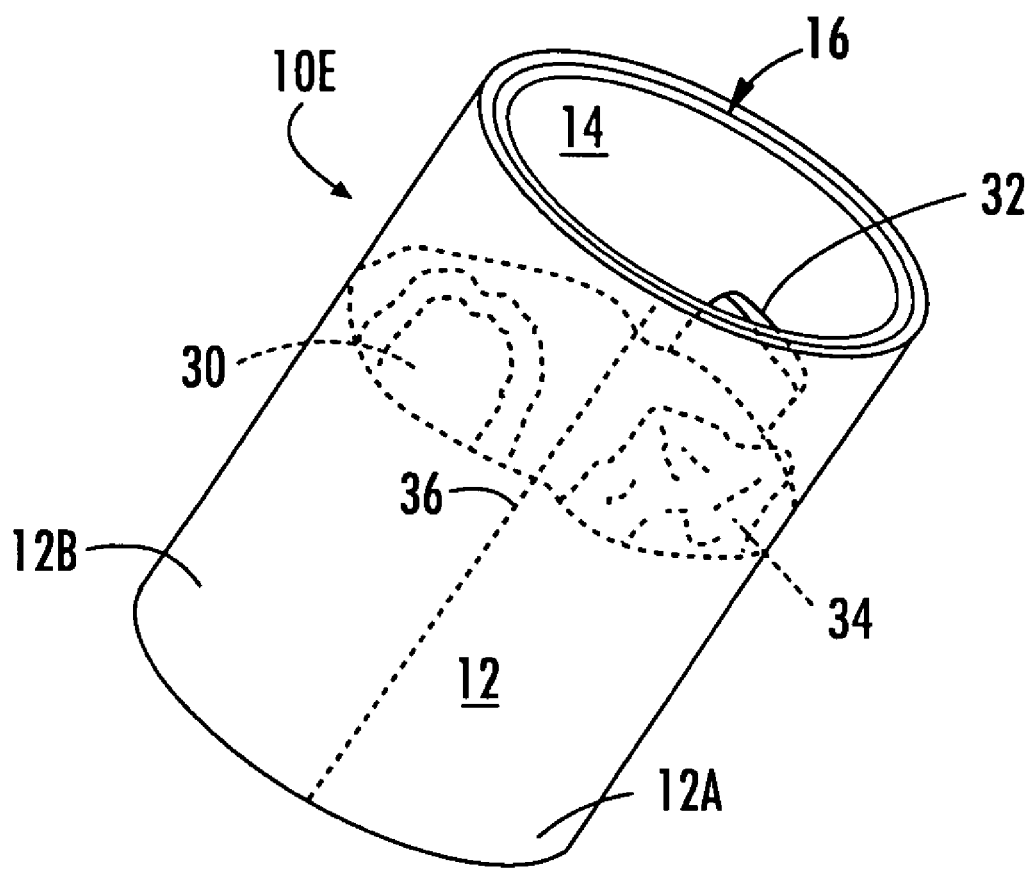
FIG. 6 is a perspective view of a personal care article as in FIG. 1 particularly showing a seamless seam according to another aspect of the invention.

With reference now to FIGS. 1, 5 and 6, the wrap 10P in this example is made from a plurality of sections 12A-F that may be panels or pieces of the same or a different material bonded or attached together seams 36 in a pattern so as to define a plurality of closed-end pocket structures 22, described above. The pockets 22 each include an opening 23 for insertion of, for example, a "tea bag" or pouch 30 containing the personal care composition 24. After one or more of the sections 12A-F are bonded or otherwise attached along the seams 36, excess materials 39 that depend from one or more of the sections can be cut adjacent to the seams 36 to form the illustrated wrap 10P. In an alternative embodiment, the sections 12A-F may be cut and bonded in a single processing step. It will be further appreciated that similar processing steps can be used to form other spa items 10 as shown in FIG. 1.

FIG. 5 particularly shows insertion of the bag 30 and one other bag 32 in respective openings 23 of respective pockets 22 to provide, for instance, aromatherapy via the personal care composition 24 in the bags 30,32. Also shown, a cold pack or ice pack 34 is inserted in one of the pockets 22 to treat an injury, for example, a swelling injury. The skilled artisan will appreciate that the ice pack 34 can be an intermediate layer permanently attached in the wrap 10P. Accordingly, the wrap 10P can be placed in a refrigerator or cooler to cool or freeze the intermediate ice pack layer for use by the user U.

FIG. 6 illustrates an embodiment in the form of an open-ended tubular structure, such as the band or sleeve 10E of FIG. 1, that includes one or more internal therapeutic layers. For example, the therapeutic layer may be disposed between elastomeric nonwoven layers or laminates.

With more particular reference to the seams 36 shown in FIGS. 5 and 6, the seams 36 are formed so as to be relatively pliable and soft to the touch without requiring additional processing such as micro-cutting. The skilled artisan will appreciate that when multiple layers of nonwovens are bonded, sometimes a seam is potentially stiff. Thus, rather than two-step bonding and die-cutting, for instance, the seam 36 is formed as an almost seamless flush seam to avoid irritating sensitive skin or body parts. Accordingly, it is not necessary to invert the article 10 after cutting along the seam 36. The seams 36 may be formed by various known techniques, particularly thermal and ultrasonic bonding methods. In accordance with one aspect of the invention, the seams 36 are formed by an ultrasonic cut-and-seal process utilizing conventional ultrasonic bonding machines in which a pattern for the articles 10 is cut from opposed sheets of materials and the panel sections are sealed in a single processing step. The width and height of the seam 36 is controlled by carefully defining the dimensions and geometry of the bonding horn or bonding anvil, or ultrasonic sewing die. The single process cut-and-seal technique is well known to those skilled in the art and a further detailed explanation thereof is not necessary for purposes of the present description.

Figure 7A:
FIGS. 7A, 7B and 7C are photomicrographs of a seam as in FIG. 6 made in accordance with aspects of the invention and particularly showing a microstructure of the seam and fiber structure.
Figure 7B:
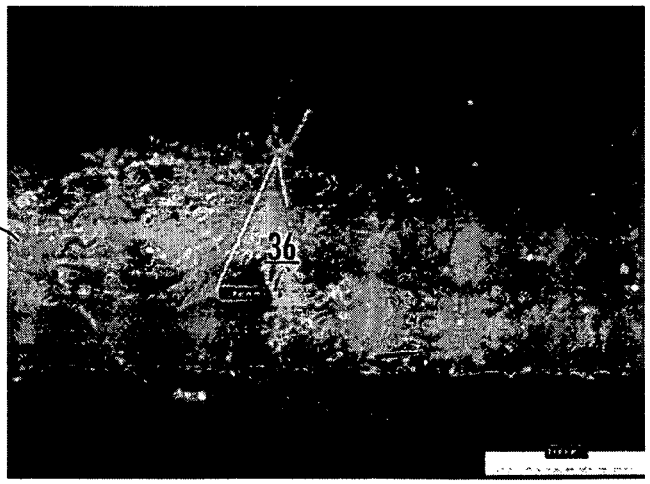
Figure 7C:
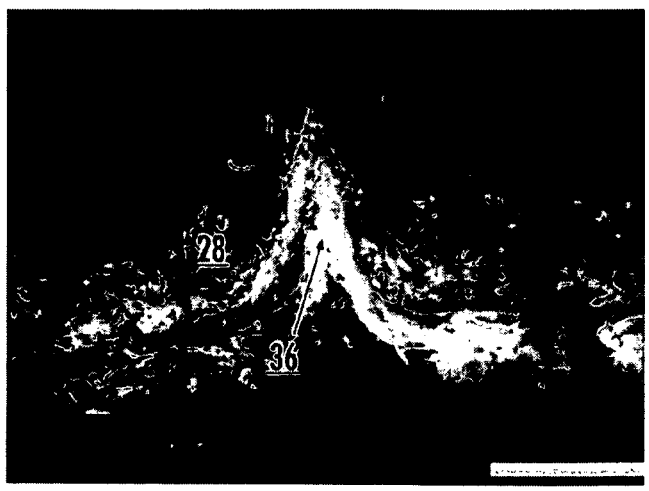

The photographs of FIGS. 7A, 7B and 7C show exemplary embodiments of seam structure wherein the seam 36 is generally less than 1 millimeter (mm) in width and 1 mm in height along generally the entire perimeter of the seam 36. In some embodiments, the seam 36 is less than 500 microns in width and 500 microns in height. In some further embodiments, the seam 36 is less than 400 microns in width and 400 microns in height. In still further embodiments, the seam 36 is less than 300 microns in width and 300 microns in height. In some further embodiments, the seam 36 is less than 200 microns in width and 200 microns in height. In yet other embodiments, the seam 36 is less than 100 microns in width and 100 microns in height, and may be less than 50 microns in width and 50 microns in height.

Stiffness of the seams 36 can be a factor of panel thickness and patterns formed in the panel material. In this regard, it may be desired not to include bonded regions of the point-bonded material in the seam 36. For instance, in the embodiment of FIG. 6, both panel sections 12A, 12B are formed from a thermally point bonded material having a border area or strip of unbonded material along the seam 36 such that the seam 36 is formed between unbonded border regions of the sections 12A, 12B. Thus, bonded regions of the materials do not add increased stiffness along the seam 36.

Referring once more to FIG. 5, to further enhance the strength and integrity of the seam 36 during donning and use of the article 10, it may be desired to include additional reinforcing welds or bond points 37 at select locations along the seam 36. For example, additional ultrasonic or thermal weld points 37 are provided adjacent to the open unsealed edges of the panel sections. These bond points 37 enhance the seam 36 at a location that may tend to separate during donning of the article 10. The bond points 37 may be formed by an additional processing step after forming the seam 36. By way of example, Yang et al. describe exemplary processes of forming "seamless" seams in U.S. patent application Ser. No. 11/118,078, filed Apr. 29, 2005, which is incorporated herein by reference thereto.

In general, the articles of the present invention can be formed from a variety of materials and can have multiple layers of materials seamlessly attached together. U.S. Pat. No. 6,647,549, incorporated herein by reference, describes various suitable materials, and combinations of materials, that may be used for the present articles. Non-limiting examples of suitable materials are described below.

Although various embodiments of the invention have been described using specific terms, devices, and methods, such description is for illustrative purposes only. The words used are words of description rather than of limitation. It is to be understood that changes and variations may be made by those of ordinary skill in the art without departing from the spirit or scope of the present invention, which is set forth in the following claims. In addition, it should be understood that aspects of the various embodiments might be interchanged either in whole or in part. Therefore, the spirit and scope of the appended claims should not be limited to the description of the preferred versions contained therein.

That which is claimed is:

1. A therapeutic article, comprising:
   a skin contact layer being configured for wear against of an appendage of a user;
   a pocket defined by the skin contact layer;
   a personal care composition disposed in the pocket so as to be in direct contact with the skin contact layer, the personal care composition having an active state and an inactive state;
   the skin contact layer being permeable to the personal care composition in the active state such that the personal care composition flows through the skin contact layer to the user's appendage;
   an external layer attached to the skin contact layer;
   a heating layer interposed between the skin contact layer and the external layer, the heating layer being configured to generate heat to activate the personal care composition from the inactive state, the external layer being configured to direct the personal care composition in the active state through the skin contact layer to treat the skin of the appendage; and
   a charcoal-containing odor control layer interposed between the skin contact layer and the external layer and is separate from said heating layer to control an unpleasant odor emanating from the personal care composition after activation of said personal care composition.

2. The therapeutic article as in claim 1, wherein the therapeutic article is an elastomeric article.

3. The therapeutic article as in claim 1, wherein the heating layer is a Far-IR emitting layer.

4. The therapeutic article as in claim 1, wherein the heating layer is a Near-IR absorbing layer.

5. The therapeutic article as in claim 1, wherein the personal care composition is selected from the group consisting of an emollient, petrolatum, mineral oil, lipid, herb, herbal extract, skin softener, aloe, anti-inflammatory product, essential oil, vitamin solution, mineral solution and combinations thereof.

6. The therapeutic article as in claim 5, wherein the essential oil is an extract selected from the group consisting of a lavender extract, tea tree oil extract, lemon grass extract, eucalyptus extract, clove extract and a thyme extract.

7. The therapeutic article as in claim 1, wherein the therapeutic article is selected from the group consisting of a facial mask, a wrap, a brace, an underarm insert, a patch, a glove, a sock, a sleeve and a girdle.

8. The therapeutic article as in claim 1, further comprising means for holding the skin contact layer against the skin, wherein the means for holding is selected from the group consisting of a snap, a hook, a pin, an adhesive, a button and hole arrangement, a hook and loop fastening arrangement, an extensible-retractive force and combinations thereof.

9. The therapeutic article as in claim 1, wherein the external layer is a reflective layer.

10. The therapeutic article as in claim 1, the external layer and the skin contact layer define a flush seam therebetween.

11. The therapeutic article as in claim 10, wherein the flush seam is less than about 300 microns in width and less than about 300 microns in height.

12. The therapeutic article as in claim 3, wherein the Far-IR emitting layer comprises a ceramic composition.

13. The therapeutic article as in claim 12, wherein the ceramic composition comprises from about 52.5 wt % to about 70 wt % silicon dioxide and from about 20 wt % to about 47 wt % aluminum oxide.

14. The therapeutic article as in claim 4, wherein the Near-IR absorbing layer comprises a thioamide compound and a compound selected from the group consisting of a copper compound, a lead compound, and combinations thereof.

15. A therapeutic article, comprising:
   a skin contact layer having a plurality of fibers forming a plurality of point-bearing surfaces configured for wear against skin of an appendage of a user;
   a personal care composition disposed in direct contact with said skin contact layer, the personal care composition having an active state and an inactive state;
   the skin contact layer being permeable to the personal care composition in the active state such that the personal care composition flows through the skin contact layer to the user's appendage;
   an external layer attached to the skin contact layer;
   a cooling layer interposed between the skin contact layer and the external layer, the cooling layer being configured to activate the personal care composition from the inactive state, the external layer being configured to direct the activated personal care composition through the skin contact layer to treat the appendage of the user;
   a charcoal-containing odor control layer interposed between the skin contact layer and the external layer that is separate from said intermediate layer and controls odors generated from activation of said personal care composition; and
   further comprising a pocket disposed adjacent the skin contact layer, the pocket being configured to contain the personal care composition.

16. The therapeutic article as in claim 15, further comprising means for holding the skin contact layer against the skin, wherein the means for holding is selected from the group consisting of a snap, a hook, a pin, an adhesive, a button and hole arrangement, a hook and loop fastening arrangement, an extensible-retractive force and combinations thereof.

17. The therapeutic article as in claim 15, wherein the external layer and the skin contact layer define a flush seam therebetween, wherein the flush seam is less than about 300 microns in width and less than about 300 microns in height.

18. A therapeutic article, comprising:
- a skin contact layer having a plurality of fibers forming a plurality of point-bearing surfaces configured for wear against skin of an appendage of a user;
- a personal care composition disposed in direct contact with said skin contact layer, the personal care composition having an active state and an inactive state;
- the skin contact layer being permeable to the personal care composition in the active state such that the personal care composition flows through the skin contact layer to the user's appendage;
- an external layer attached to the skin contact layer, the external layer and the skin contact layer defining a flush seam therebetween;
- a Far-IR emitting intermediate layer comprising a ceramic composition and interposed between the skin contact layer and the external layer, the intermediate layer being configured to activate the personal care composition from the inactive state, the external layer being configured to direct the activated personal care composition through the skin contact layer to treat the appendage of the user;
- an odor control layer interposed between the skin contact layer and the external layer that is separate from said intermediate layer and controls odors generated from activation of said personal care composition; and
- further comprising a pocket disposed adjacent the skin contact layer, the pocket being configured to contain the personal care composition.

19. The therapeutic article as in claim 18, wherein the therapeutic article is selected from the group consisting of a facial mask, a wrap, a brace, an underarm insert, a patch, a sock, a sleeve and a girdle.

20. The therapeutic article as in claim 18, wherein the flush seam is less than about 300 microns in width and less than about 300 microns in height.

21. The therapeutic article as in claim 18, wherein the ceramic composition comprises silicon dioxide and aluminum oxide.

22. The therapeutic article as in claim 21, wherein the silicon dioxide comprises from about 52.5 wt % to about 10 wt % of the ceramic composition and the aluminum oxide comprises from about 20 wt % to about 47 wt % of the ceramic composition.

23. The therapeutic article as in claim 18, wherein the odor control layer is a charcoal-containing odor control layer.

24. A therapeutic article, comprising:
- a skin contact layer having a plurality of fibers forming a plurality of point-bearing surfaces configured for wear against skin of an appendage of a user;
- a personal care composition disposed in direct contact with said skin contact layer, the personal care composition having an active state and an inactive state;
- the skin contact layer being permeable to the personal care composition in the active state such that the personal care composition flows through the skin contact layer to the user's appendage;
- an external layer attached to the skin contact layer, the external layer and the skin contact layer defining a flush seam therebetween;
- a Near-IR absorbing intermediate layer comprising a thioamide compound and a compound selected from the group consisting of a copper compound, a lead compound, and combinations thereof, and interposed between the skin contact layer and the external layer, the intermediate layer being configured to activate the personal care composition from the inactive state, the external layer being configured to direct the activated personal care composition through the skin contact layer to treat the appendage of the user;
- an odor control layer interposed between the skin contact layer and the external layer that is separate from said intermediate layer and controls odors generated from activation of said personal care composition; and
- further comprising a pocket disposed adjacent the skin contact layer, the pocket being configured to contain the personal care composition.

25. The therapeutic article as in claim 24, wherein the therapeutic article is selected from the group consisting of a facial mask, a wrap, a brace, an underarm insert, a patch, a sock, a sleeve and a girdle.

26. The therapeutic article as in claim 24, wherein the flush seam is less than about 300 microns in width and less than about 300 microns in height.

27. The therapeutic article as in claim 24, wherein the odor control layer is a charcoal-containing odor control layer.

* * * * *